United States Patent [19]

Kirmann

[11] Patent Number: Plant 6,022

[45] Date of Patent: Sep. 22, 1987

[54] GERANIUM PLANT NAMED LILLY

[75] Inventor: Wolfgang Kirmann, Langenzersdorf, Austria

[73] Assignee: Mirko Vavra, Bisamberg, Austria

[21] Appl. No.: 810,704

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Lilly having violet-red flower color, variegated with dark purple; early flowering; good bud production at night temperatures up to 16° C., thus providing a long and continuous flowering period; ease of propagation and good rooting habit; compact growth habit; good resistance against parasites.

2 Drawing Figures

The present invention comprises a new and distinct cultivar of geranium, botanically known as *Pelargonium domesticum,* and hereinafter referred to by the cultivar name Lilly.

Lilly is a product of a planned breeding program which had the objective of creating new geranium cultivars having compact growth habit, early flowering, long lasting flowers, good flower production, relatively small foliage, good resistance against parasites, and bright violet-red flower color.

Lilly was originated from a hybridization made by applicant in a controlled breeding program in Bisamberg, Austria in 1978. The female parent was a cultivar designated as seedling 8/73 having a compact growth habit and single lilac flowers. The male parent of Lilly was Fruhling/75, a cultivar similar to the variety Fruhling but with more stable foliage and lighter colored petals.

Lilly was discovered and selected as one flowering plant within the progeny of the stated cross by applicant on Feb. 2, 1977 in a controlled environment in Bisamberg, Austria.

The first act of asexual reproduction of Lilly was accomplished when vegetative cuttings were taken from the initial selection on Aug. 29, 1977 in a controlled environment in Bisamberg, Austria by a technician working under formulations established and supervised by Wolfgang Kirmann. Horticultural examination of selected units initiated in the spring of 1978 has demonstrated that the combination of characteristics as herein disclosed for Lilly are firmly fixed and are retained through successive generations of asexual reproduction.

Lilly has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Lilly, which in combination distinguish this geranium as a new and distinct cultivar.

1. Bright violet-red flower color, variegated with dark purple.

2. Early flowering response and long flowering period.

3. Propagates well, with very good rooting habit.

4. Medium green foliage.

5. Compact growth habit; good bud production.

6. Good resistance against parasites, particularly white fly.

7. Tolerance to overwatering in cultivation.

8. Buds are produced under normal greenhouse conditions (5000 Lux for 16 hours per day) at 14°–16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.

9. Lilly is unique with regard to the combined features of compactness, continuous flowering, floriferous habit, and violet-red flower color.

Of the many commercial cultivars known to the present inventor, the most similar in comparison to Lilly is Fruhling, an unpatented but commercial cultivar. In comparison to Fruhling, Lilly has a more compact growth habit, earlier and more continuous flowering, different flower color, and more stable foliage.

The accompanying photographic drawings show typical flower and foliage characteristics of Lilly, with colors being as true as possible with illustrations of this type.

Sheet 1 is a perspective view of a potted plant of Lilly.

Sheet 2 is a black and white print showing the upper surface of immature and mature plants of Lilly.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.—Pelargonium domesticum.*

*Commercial.*—Commonly referred to as a "Martha Washington" geranium, and having the cultivar name Lilly.

INFLORESCENCE

A. Umbel:

*Average diameter.*—Relatively small, 85–95 mm.
*Peduncle length.*—Normal.
*Pedicel length.*—Normal.

B. Corolla:
*Average diameter.*—55–65 mm; total inflorescence diameter is well within the foliage.
*Form.*—5 petals, symmetric; generally round.
*Color (general tonality from a distance of three meters).*—Violet red, with small, dark purple variegation on upper two petals.
*Color (upper surface).*—63B-60D, throat showing 59A.

C. Bud:
*Shape.*—Oval.
*Color.*—Lilac.

D. Reproductive Organs:
*Androecium.*—Yellow, 7–9 stamens.
*Gynoecium.*—Five to eight lobed stigma.

E. Spring flowering response period: Very early.

F. Durability: Good.

PLANT

A. Foliage:
*Form.*—Zygomorphic with a nectar spur.
*Margin.*—Crenate.
*Color (upper surface).*—Medium green.
*Tolerance of Botyrtis and soil fungi.*—Good.

B. General appearance and form:
*Internode length.*—Medium short.
*Branching pattern.*—Good.
*Height.*—Compact.

I claim:

1. A new and distinct cultivar of geranium named Lilly, as described and illustrated, and particularly characterized by its violet-red flower color, variegated with dark purple; early flowering; good bud production at night temperatures up to 16° C., thus providing a long and continuous flowering period; ease of propagation and good rooting habit; compact growth habit; and good resistance against parasites.

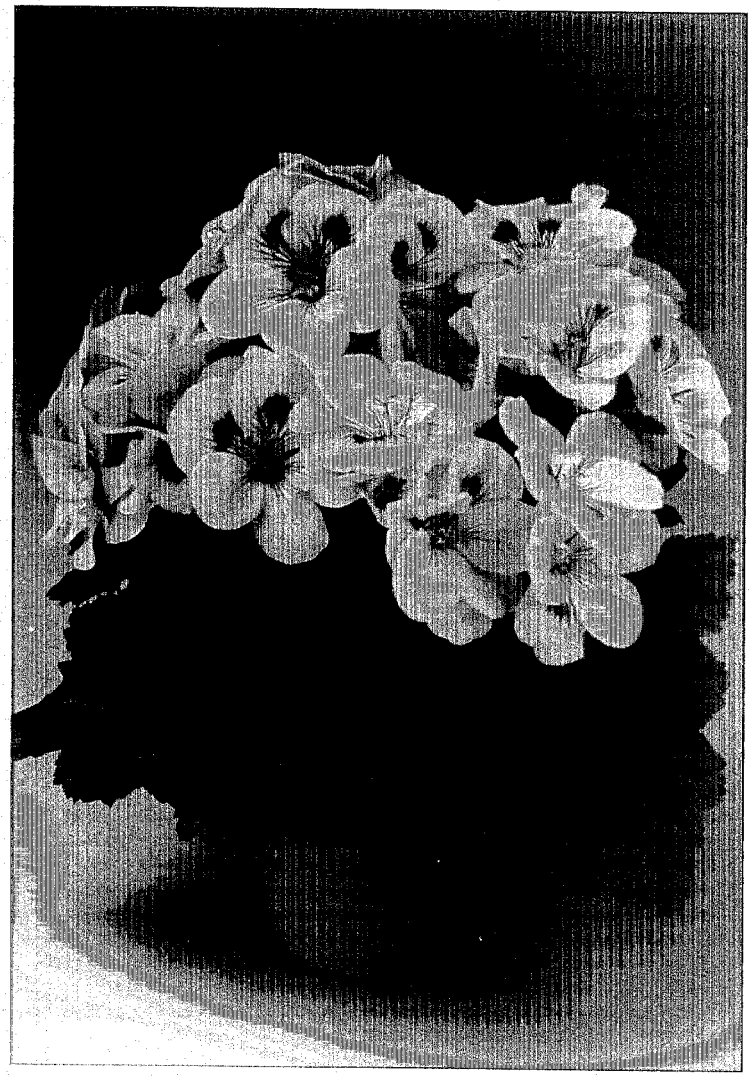

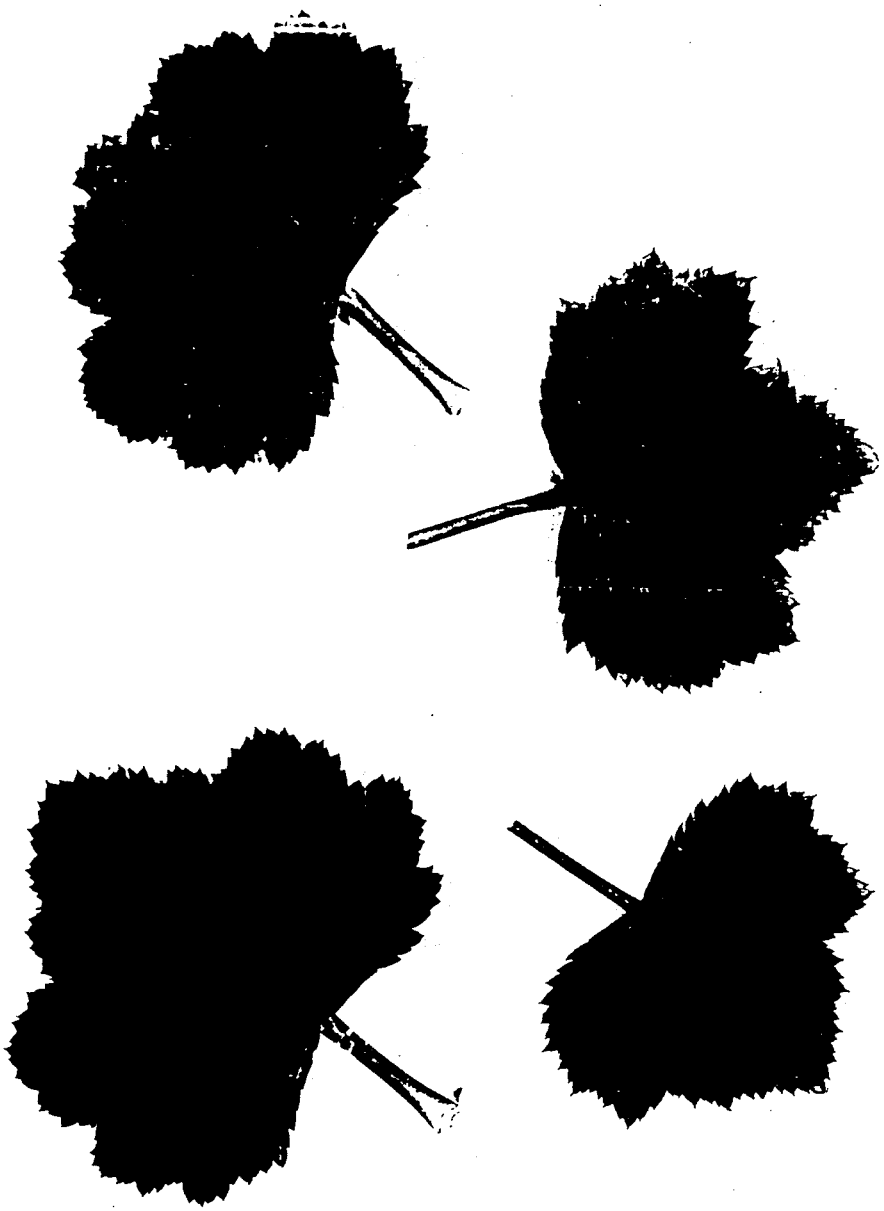

* * * * *